(12) United States Patent
Youngbull et al.

(10) Patent No.: US 11,639,934 B2
(45) Date of Patent: May 2, 2023

(54) APPARATUS AND METHOD FOR THE DETECTION OF BIOAEROSOLS

(71) Applicant: University of Montana, Missoula, MT (US)

(72) Inventors: Aaron Cody Youngbull, Kalispell, MT (US); Timothy Burgin, Scottsdale, AZ (US)

(*) Notice: Subject to any disclaimer, the term of this patent is extended or adjusted under 35 U.S.C. 154(b) by 242 days.

(21) Appl. No.: 17/271,494

(22) PCT Filed: Aug. 30, 2019

(86) PCT No.: PCT/IB2019/001452
§ 371 (c)(1),
(2) Date: Feb. 25, 2021

(87) PCT Pub. No.: WO2020/148566
PCT Pub. Date: Jul. 23, 2020

(65) Prior Publication Data
US 2021/0199656 A1    Jul. 1, 2021

Related U.S. Application Data

(60) Provisional application No. 62/725,806, filed on Aug. 31, 2018.

(51) Int. Cl.
| | |
|---|---|
| *G01N 33/569* | (2006.01) |
| *G01N 1/22* | (2006.01) |
| *G01N 15/06* | (2006.01) |
| *G01N 33/543* | (2006.01) |
| *G01N 15/00* | (2006.01) |

(52) U.S. Cl.
CPC ......... *G01N 33/569* (2013.01); *G01N 1/2202* (2013.01); *G01N 15/0606* (2013.01); *G01N 33/54346* (2013.01); *G01N 2001/2223* (2013.01); *G01N 2015/0088* (2013.01)

(58) Field of Classification Search
CPC .............. G01N 33/569; G01N 1/2202; G01N 15/0606; G01N 33/54346; G01N 2001/2223; G01N 2015/0088; G01N 1/22; G01N 33/54313; G01N 33/582; G01N 1/2273
See application file for complete search history.

(56) References Cited

U.S. PATENT DOCUMENTS

| | | |
|---|---|---|
| 8,539,840 B2 | 9/2013 | Ariessohn et al. |
| 2004/0191765 A1 | 9/2004 | Mozdy et al. |
| 2004/0232052 A1 | 11/2004 | Call et al. |
| 2013/0042893 A1* | 2/2013 | Ariessohn ............ G01N 1/2202 137/560 |

FOREIGN PATENT DOCUMENTS

WO    2008048300 A2    4/2008

OTHER PUBLICATIONS

International Preliminary Report on Patentability, International Application No. PCT/IB2019/001452, dated Mar. 2, 2021, 8 pages.
International Search Report, International Application No. PCT/IB2019/001452, dated Jul. 3, 2020, 4 pages.

* cited by examiner

*Primary Examiner* — Jennifer Wecker
*Assistant Examiner* — Oyeleye Alexander Alabi
(74) *Attorney, Agent, or Firm* — Glenn H. Lenzen; Elevated IP, LLC

(57) ABSTRACT

An autonomous bioaerosol sampling and detection system and method adapted to provide real-time detection and identification of bio-organisms in aerosols without human intervention.

18 Claims, 2 Drawing Sheets

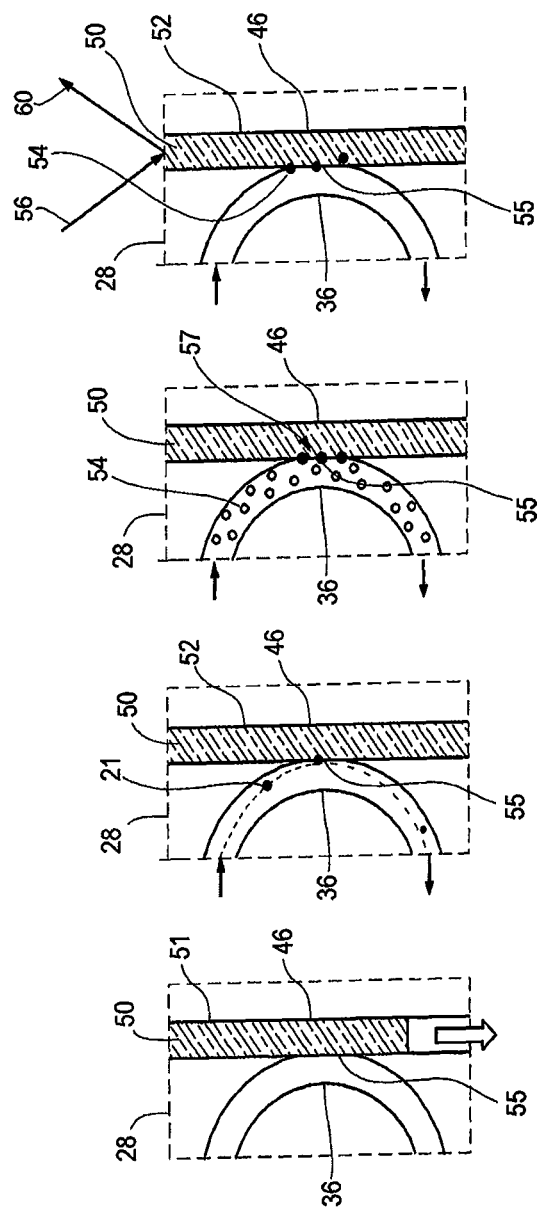

APPARATUS AND METHOD FOR THE DETECTION OF BIOAEROSOLS

CROSS-REFERENCE TO RELATED APPLICATIONS

This application claims priority to International Application No. PCT/IB2019/001452, filed Aug. 30, 2019, which claims priority U.S. Provisional Patent Application No. 62/725,806 filed Aug. 31, 2018, the entire disclosures of which are incorporated herein by reference.

FIELD OF THE INVENTION

The present invention relates to the detection of biological substances in aerosols. More specifically the present invention relates to an apparatus and method for the rapid detection, capture, identification and quantization of bioaerosol organisms.

BACKGROUND OF THE INVENTION

Aerosols have long been recognized as potential carriers of biological materials and organisms that may be human health hazards. Aerosols are suspensions of fine solid particles or liquid droplets in air or a carrier gas. Aerosols also may be enclosed in a container under pressure and released with a propellant gas in the form of a directed stream of a suspension toward a specific target. Examples of commonly used aerosols include cosmetics, insect sprays, cleaning agents and air fresheners, to name a few.

Hazardous bio-organisms may include, for example, molds, anthrax, and tuberculosis or, in the case of chemical and biological warfare and terrorist activity, pathogenic agents designed to incapacitate or kill targeted population groups. Defenses to potentially devastating biochemical or hazardous pathogenic attacks must be capable of rapid deployment under field conditions. However, a necessary precursor to implementation of countermeasures is the swift and accurate detection, identification and quantification in the field of target biohazard organisms that may be aerosol-borne.

Current commercial solutions to the identification of a target organism in a bioaerosol system involve separate capture and analysis steps. The method of analysis is typically a polymerase chain reaction (PCR) based amplification of a target DNA/RNA sequence and subsequent detection. This process requires cell lysis, and the chemical amplification step takes time. In addition, the presence of inhibitors can complicate detection.

Positive identification of a target organism or pathogenic agent often requires multiple means of identification. Therefore sequential down selection of aerosol particles, coupled with identification of multiple epitopes on the target organism is necessary. In some instances, detection of a single organism is desired. Current detection and identification of bioaerosols is a multistep process requiring human intervention at various points of the process. The currently available detection systems also require preprocessing of the collected biologicals to enable detection; however, they also lack the sensitivity to detect a single organism without chemical amplification, which, as noted above, requires additional time.

Two types of bioaerosol detectors are currently in use. The first type of bioaerosol detector establishes the presence of biological material but provides little or no information as to the organisms present. Examples of this type of sensor include fluorescent sensors based on the fluorescence of optically excited biological molecules, Raman spectroscopy, light scattering, and other techniques known in the art. The second type of sensor identifies species-specific markers of a target organism, thereby allowing the unique identification of the organism. Examples of this type of sensor are polymerase chain reaction techniques (PCR), as well as mass spectroscopy. However, none of these prior art devices and methodologies address the requirements for a rapid, field deployable, system for the real-time identification and quantification of biohazard organisms that may be aerosol-borne.

In view of the above, it will be apparent to those skilled in the art from this disclosure that a need exists for an improved field-deployable system and method for the rapid and accurate detection, identification and quantification of bioaerosols. The present invention addresses these needs in the art as well as other needs, all of which will become apparent to those skilled in the art from the accompanying disclosure.

SUMMARY OF THE INVENTION

To address the needs in the art, one aspect the present invention provides an autonomous bioaerosol sampling and detection system adapted to provide real-time detection and identification of bio-organisms in aerosols without human intervention.

In another aspect of the present invention, a highly sensitive, autonomous bioaerosol sampling and detection system is provided which is capable of identifying single specific bio-organism targets by identifying multiple epitopes associated with the specific target bio-organism.

In still another aspect of the present invention, an autonomous bioaerosol sampling and detection system is provided which may be configured to perform either multiple parallel or serial analyses of bioaerosol samples.

In yet another aspect of the present invention, an autonomous bioaerosol sampling and detection system is provided which may be adapted for either continuous or on-demand analysis of target bioaerosol organisms.

In another aspect of the present invention, an autonomous bioaerosol sampling and detection system is provided which provides real-time or near real-time detection of targeted bio-organisms in the field.

In an aspect of the present invention, an autonomous bioaerosol sampling and detection system is provided which includes upconverting nanocrystal probes that attach to target bio-organism epitopes.

In yet another aspect of the present invention, an autonomous bioaerosol sampling and detection system is provided having at least one optical excitation/detection head adapted to detect and excite upconverting nanocrystal probes attached to target bio-organism epitopes.

In another aspect of the present invention, a method of rapid detection, identification and quantization of target bio-organisms in aerosols is provided which detects post-excitation energy released by preselected upconverting nanocrystal probes attached to the target bio-organisms.

These and other features, aspects and advantages of the present invention will become apparent to those skilled in the art from the following detailed description of preferred embodiments taken in connection with the accompanying drawings and by reference to the appended claims.

BRIEF DESCRIPTION OF THE DRAWINGS

Referring now to the attached drawings which form a part of this original disclosure.

FIG. 2.A. is an enlarged plan view of a centrifugal particle trap portion of the bioaerosol detection device of FIG. 1 showing the air inlet in a closed position in accordance with an embodiment;

FIG. 2.B. is an enlarged plan view of the centrifugal particle trap portion of the bioaerosol detection device of FIGS. 1 and 2.A. showing the air inlet in an open position to introduce target particulates into the inlet channel;

FIG. 2.C. is an enlarged plan view of the centrifugal particle trap portion of the bioaerosol detection device of FIGS. 1, 2.A. and 2.B. showing the introduction of fluorescent antibody up-converting nanocrystals (UNC's) into the inlet channel; and FIG. 2.D. is an enlarged plan view of the centrifugal particle trap portion of the bioaerosol detection device of FIGS. 1, 2.A., 2.B. and 2.C. showing the infrared excitation of UNC's that are bound to target particulates in accordance with an embodiment.

DETAILED DESCRIPTION OF THE PREFERRED EMBODIMENTS

Figure 1:
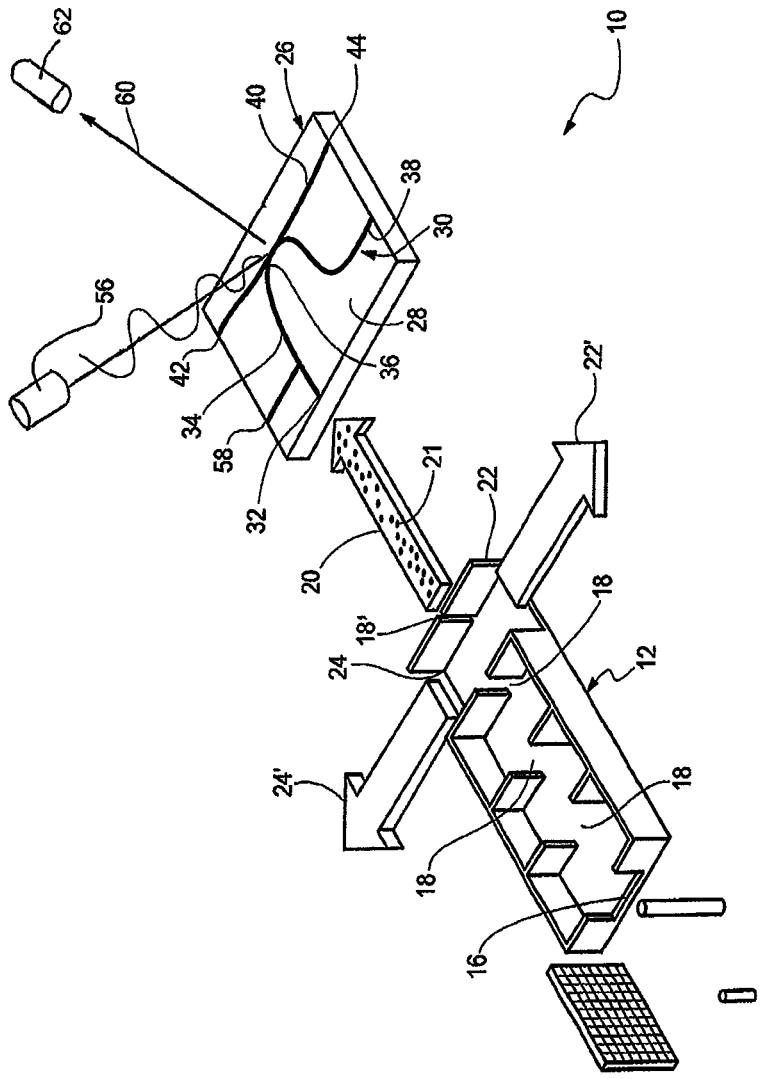
FIG. 1 is a perspective view of the elements of a bioaerosol detection device in accordance with an embodiment of the present invention.

The following detailed description illustrates the invention by way of example and not by limitation. The description will clearly enable one skilled in the art to make and use the invention and its methodology and describes several embodiments, adaptations, variations, alternatives and uses of the invention.

Referring now to FIG. 1, the elements of a detection apparatus or device 10 for the autonomous real-time or near real-time sampling and detection of aerosol-borne bio-organisms are illustrated. More general elements not shown in the figure include a front blower, embedded electronics (controls, power, and data), a specific light source and detector, a reagent storage bay, and instrument housing. The device 10 includes an aerodynamic lens (ADL) or focusing mechanism 12 structured and arranged to sample and collect via inlet 16 large volume specimens or samples of inlet air containing aerosol particles and bio-organisms, the particles and bio-organisms being in a preselected size range. The focusing mechanism or ADL is an enclosed device which directs the inlet air and aerosol through a plurality of spaced-apart apertures 18 that progressively and sequentially decrease in size. The apertures are structured and arranged to simultaneously focus or concentrate the air and the aerosol particles and/or bio-organisms within a preselected size range into a spatially confined and controlled particle beam 20 containing aerosol particles and/or bio-organisms 21 of interest. The remaining non-selected air containing aerosol particles and/or bio-organism falling outside the preselected size range is discharged from the device via discharge ports 22, 24 as indicated by the arrows 22' and 24'.

The spatially confined particle beam 20 is directed via a narrowest of the spaced-apart apertures 18' to a centrifugal particle trap assembly (CPT) or microfluidic chip 26 which is adapted to further downselect the particles of interest by size and to capture them for analysis. The trap includes a body 28 having a microfluidic channel shown generally at 30 formed therein. The microfluidic channel has an inlet 32 adapted to receive the spatially-confined particle beam 20, a U-shaped channel section 34 operatively connected to the inlet 32, the channel including a centrifugal particle trap section 36 adapted to capture aerosol particles in a preselected target size range, and an aperture 38 outlet connected to the trap section for discharging the spatially-confined particle beam 20 after sampling, as will be described in greater detail below.

Referring now to FIGS. 2.A.-2.D., the body 28 of the trap assembly or chip 26 further includes a cross-channel 40 extending in a direction generally transversely to the direction of the portion of the microfluidic channel operatively connected to the inlet. The cross-channel includes an inlet 42, an outlet 44 and a midsection 46, which is adapted to be in fluid communication with the microfluidic channel via an aperture or window 55 disposed there between. A renewable wetted hydrogel-coated fiber-based sensor material or platform, for example, a polymer thread 50 loaded with a gel matrix 51 containing appropriate capture and sensing probes or antibodies 52, is movably positioned in the cross channel 40, as indicated by the directional arrow in FIG. 2.A. The cross channel is structured such that the midsection 46 tangentially intersects the U-shaped channel 34, thereby forming the aperture or window 55 in the U-shaped channel. The aperture 55 exposes the particle beam to the adjacent hydrogel-coated fiber in the cross channel and creates an impact or detection zone 57 (FIG. 2.C.) where the particle beam makes contact with the hydrogel coated polymer thread 50. The capture and sensing antibodies 52 in the gel are selected based upon their affinity for attaching to the target bioaerosol particles and/or bio-organics. The fiber can be pulled through the cross channel to expose fresh hydrogel as needed in the impact zone of the centrifugal trap.

As best shown in FIG. 2.B., as the particle beam 20 flows through the centrifugal particle trap 36 and through the window 55, the down-selected particles 21 are embedded in the gel matrix and are captured by the capture or antibody probes. Referring to FIG. 2.C., once the particles are captured, the impact or detection zone 57 is washed to remove unwanted particles and exposed to preselected upconverting nanocrystal (UNC) sensing probe(s) 54. After a final rinsing step to remove unbound probes, the captured particles are optically interrogated via energy from an excitation energy source or head, shown generally at 56. UNCs exhibit zero background autofluorescence, have significant photonic amplification capability, and do not photo-bleach, thus permitting single organism detection. An upstream flow path, labelled 58 in FIG. 1 positioned in microfluidic chip 26 upstream of the enlarged channel region shown in FIG. 2, allows rinsate and the antibody-UNCs to be introduced or delivered through the U-shaped channel to the target bioaerosol particles after the particles have been immobilized in the antibody-laden gel. An energy detection device 62 may be used as either a yes/no indicator of the presence of the target organism or to quantitate the amount of organism present. The energy released by the UNC's following excitation/optical interrogation is indicated at 60 in FIGS. 1 and 2.D. This energy, which is indicative of a detection event, is subsequently transmitted to a remote receiver (not shown) via wireless communication, as is known in the art.

The apparatus is designed to be adaptable to numerous detection methodologies. Many different types of biochemical probes and reactions may be supported by the device by sequential introduction of reagents and/or thermal profiles. In this sense, the instrument is a biochemical detection platform that brings together optimal sampling and multi-stage down-selection by delivering specific bioaerosol targets to the sensing region while physically excluding background interference in the form of unwanted particles.

FIGS. 2.A.-2.D. outline more specifically the principal biosensing procedure or method in the present invention The procedure employs an antibody-based approach having optimal sensitivity, specificity, and multiplex capability utilizing a refreshable capture and sensing gel. In sandwich-ELISA (enzyme-linked immunosorbent assay) processing, at least two different antibodies are used, each designed for different epitopes on a target bioaerosol, a feature which increases specificity. One antibody is fixed on a surface of an element of the device and the other is bound to a mobile fluorescent label. In the device and the associated detection methodology of the present invention, as described above, the fixed antibody is linked to a refreshable hydrogel coated fiber 50 that is pulled through the device. By sequential introduction of the target, marker reagents, fiber surface, and washing steps, the target bioaerosol becomes optically identifiable at the location in the microfluidic chip. More specifically, upconverting nanocrystals (UNCs) 54 serve as the fluorescent label normally used in the ELISA process. Typically, sandwich-ELISA requires hours of incubation to allow for the target and antibody-conjugates to commingle via diffusion. However, using the novel process of the present invention, the combination of the microfluidic channel and the UNC reporter allow for rapid association (in terms of minutes) and trace single colony forming unit (cfu) detection of the target bioaerosol. Once a positive or negative detection event has occurred, the sensor material in the microfluidic chip is refreshed. With this approach, detection could reasonably be repeated on a few-minute interval basis using only tens of microliters of reagents per cycle.

As noted above, within the device, two independent flow paths converge in the optical sensing region: a U-shaped channel 34 that acts as a centrifugal particle trap (CPT) 36 to capture aerosol particles of the target size, and a cross-channel 40 that brings refreshable material into the impact zone 57 formed by the window 55 of the centrifugal trap. The upstream flow path 58 facilitates introduction of the rinsate and the antibody-UNCs through the U-shaped channel after the target bioaerosols have been immobilized in the antibody-laden gel. FIGS. 2.A.-2.D. represent a 'single-chamber' approach but it is also possible to pull the impact matrix through a series of chambers for each step.

In another embodiment, unbound antibody-labelled UNC marker(s) are included in the gel matrix, potentially allowing simultaneous capture and labeling of the target and requiring only a single rinsing step. Aggregate response multiplex detection is achieved by using any number of unique antibodies in the gel together with different color UNC antibody markers. Parallel multiplex of six or more targets is achievable using this approach. Sequential multiplex is also possible when knowledge of the relative concentration of various targets is required. A unique antibody for each target epitope, serially introduced in the cross-channel, would be necessary in this case. Fresh antibody-laden gel is introduced at each sensing cycle. By closing off the U-shaped channel at both its inlet and its outlet, and then pulling the gel through the cross-channel (as opposed to pushing it through), the gel will remain isolated within the cross-channel, and the U-shaped channel will remain clear for the centrifugal particle trap to properly function.

The cross-channel material will be an aqueous polymeric gel, comprised of antibody conjugated to chemically cross-linked polyacrylic acid. The gel is prepared through radical polymerization of methyl acrylate and divinylglycol, followed by acid hydrolysis to form the polyacrylic acid. Surface derivatization of the polymer as a succinimidic ester, followed by coupling to the desired antibody will provide the desired polymer-antibody conjugate. The coupling methodology is general and can be applied to the desired antibody without prior antibody functionalization.

The fluorescent marker that binds to the immobilized target microbes in the gel is a water-soluble upconverting nanocrystal (UNC). The UNCs are surface functionalized with antibodies for specific, free epitopes on the bound microbes. UNCs are necessary to reduce the lower-limit of detection and increase signal over the auto-fluorescent background of the polymer gel and microbes themselves. Single cfu sensitivity is an important element of the rapid response time of the system. Near-infrared energies are incapable of exciting anything in the device or environment other than the UNCs. The use of near-infrared excitation energy also allows for excitation through a channel cover glass which may be many millimeters thick.

By way of example and not of limitation, an optical detection head may be in the form of a fluorescence microscope flow-cell detector that surrounds the refreshable CPT micro fluidic component. However, it is to be understood that other field-deployable instrumentation may be used without departing from the scope of the instant invention.

The essential design of an exemplary optical excitation/detection head follows that of a standard epi-illumination fluorescence microscope but in a compact, self-contained unit coupled to a microfluidic device. A single commercial-off-the-shelf objective lens focuses LED illumination, or, for example, laser excitation, and collects emission and reflections onto an integrating, low-noise, high-speed photomultiplier tube and spatial imaging camera, all through the same lens. The lens is a flat-field, infinity-corrected lens having a high numerical aperture which allows for light sources and filters to be easily combined through stacked dichroic filter cubes behind the back aperture of the objective. The microfluidic chip element of the head is mounted directly to the objective lens with a custom mounting bracket that allows fine 3D positioning of the chip relative to the focal spot post-assembly. The ability to adjust focal spot on the chip allows for the system to be optimally aligned regardless of manufacturing tolerances in the optical assembly, microfluidic chip, and mounting brackets. The optical detection head will be robust against rapid accelerations and impact, and it is imminently field deployable.

Within the optical detection head, a commercial-off-the-shelf, single-mode excitation laser may be used to illuminate the detection region through a tight-focus, long-working distance objective lens. Fluorescence emission from the target is collected through the same objective with no loss of sensitivity, since there will be no autofluorescence and no near-infrared sensitivity on the detector. In this example, the detector element is a photomultiplier tube (PMT) module with peak sensitivity in the visible portion of the spectrum. A custom manufactured filter cube is used to hold the dichroic and emission filters as well as mount the excitation sources 56 (laser and broadband LED), detectors 62 (PMT and imaging camera), and the objective lens. Multiple filter cubes and PMTs are used when multiplex detection is required. Another custom manufactured part is used to attach the microfluidic chip to the objective lens barrel in an adjustable fashion with 3-degrees of freedom in order to optimize the system regardless of manufacturing and assembly tolerances in the microfluidic chip and optomechanical components. Custom production of these optomechanical components allows the optical detection head to have a small footprint.

UNCs are fundamentally non-linear in their response with an activation energy sufficient to visually detect a single nanocrystal, the intensity being on the order of only a few milliwatts per millimeter squared. Increasing the excitation power increases the UNC emission rate exponentially and does not critically disrupt the target or the background, since these do not comparatively absorb the near-infrared energy in a manner similar to the absorption characteristics of the UNC. With a tightly-focused optical detection head, the excitation spot is only a few microns in diameter. Accordingly, near-infrared lasers have more than sufficient power to excite and observe the presence of even a single UNC. The target detection signal, i.e. the voltage of the PMT above some calibrated threshold, will be processed and sent by the instrument wirelessly via the desired communications protocol. A small CMOS camera and broadband LED integrated with the detection head may also provide visual feedback on the status condition of the microfluidic channel. Visual feedback together with additional fluid level/flow sensors and electrical current sensors are used in any robust microfluidic field device to allow for automated response to anticipated failure and nominal operation modes such as clogging, bubbles, leaks, consumable levels, electrical shorts, etc. Such status conditions can also be communicated wirelessly by the instrument to indicate when service is required.

The biochemical affinity reagents to be used in the device and in the method of the present invention are either UNC-labelled antibodies or aptamer probes. However, probe-free methods such as auto fluorescence and Raman detection may also be used successfully. Both antibodies and aptamers are commercially available for common bioaerosol targets. The use of surface bound antibodies, which irreversibly bind to immobilized targets, requires a rinse step to remove unbound targets and/or markers. Antibodies are well established, rapid and specific post-capture reporters for a wide variety of biological targets. However, the use of aptamer probes, with their "turn-on" hybridization capability, allows for either their pre-embedment in the gel matrix, or for their introduction after target impaction and immobilization. Aptamer probes would not require any additional rinsing steps after association with the target. Aptamers are additionally attractive as they can be produced at industrial scale, require no refrigeration, and are readily lyophilized (freeze-dried) within the hydrogel matrix for long term storage prior to use in the field. In view of the foregoing, one may appreciate that the device is adaptable to numerous existing and potential future sensing methodologies. The instrument is designed to operate autonomously, with either capture on demand, or continuous operation modes available.

An exemplary process flow for the system is as follows:

1) An optional electrostatic precipitation pre-filter removes large particles and other materials outside the size range of the target bioaerosol. A major source of instrument failure is clogging from such debris and a standard, physical pre-filter would need regular replacement and be a potential biohazard.

2) Contaminated air is passed through an aerodynamic lens (ADL) to concentrate the desired particulate matter to a nearly monodisperse size distribution. The size and morphology of the ADL is specific to the size range of the target bioaerosol which can range from a few nanometers to one hundred microns in diameter. Alternative sizes can be accommodated without any significant change to the instrument development plan. Multiple ADLs can be deployed in parallel for broad target addressability. 5 micron diameter bioaerosols is the average size of pathogenic inhalants. Particles outside the selected size range are expelled from the ADL, without clogging, through the major flow outlets.

3) The target-enriched, controlled particle beam from the ADL is passed through a microfluidic optical channel having a tight bend radius. Because of this tight radius, the target bioaerosol impacts and sticks to a gel matrix in a process known as Centrifugal Particle Trapping (CPT). CPT has a higher collection efficiency over a broader size distribution as compared to a physical filter, separates particles by size, obviates blockage, and increases viability of biological particles captured in the trap.

4) Upconverting antibody-probes introduced via the upstream flow path 58 (or coated on the antibody gel matrix for assay flexibility) associate to the now immobilized target with high specificity. This common biosensing procedure, to use immobilized probes to first trap a biotarget and then optically label the trapped target with at least one additional, fluorescent probe, is known as a "Sandwich" Enzyme-Linked ImmunoSorbent Assay (ELISA). ELISA requires wash steps to remove unbound non-specific particulates. ELISA typically requires many hours of incubation to associate the antibodies with the target epitopes but the system and method of the present invention avoid this delay by using closed microfluidic volumes and upconverting fluorescent markers. The microfluidic chamber reduces the diffusion time of the particulates and upconverters lower the limit of detection so that only a single-probe is required to irreversibly associate with the target.

5) The result of the analysis is automatically transmitted to a remote location via wireless communication.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for limiting the invention as defined by the appended claims and their equivalents.

What is claimed is:

1. A system for the sampling and detection of target bio-organisms in aerosols, the system comprising:
   an aerodynamic lens, the lens including an inlet adapted to receive air samples containing aerosol particles and bio-organisms of interest, the particles and bio-organisms being in a preselected size range;
   a focusing mechanism adapted to concentrate the air samples into a spatially-confined and controlled particle beam, the focusing mechanism including an outlet and at least one port adapted to discharge air samples containing aerosol particles and bio-organisms of sizes that fall outside the preselected size range;
   a particle trap assembly or microfluidic chip operatively connected to the focusing mechanism; the microfluidic chip including a body portion;
   a microfluidic channel formed in the body portion of the particle trap assembly, the microfluidic channel including an inlet adapted to receive the particle beam, the channel having a U-shaped portion operatively connected to the inlet, a centrifugal particle trap section, and an outlet operatively connected to the particle trap section trap section and adapted to discharge the spatially-confined particle beam;
   a cross channel having an inlet, an outlet and a midsection positioned intermediate the inlet and the outlet, the midsection being in fluid communication with the microfluidic channel;

a sensor material or platform movably positioned in the cross channel, the sensor material including a plurality of capture or sensing antibodies adapted to attach to the target bio-organisms;

a plurality of up-converting antibody nanocrystal (UNC) sensing probes or markers adapted to bind with the target bio-organisms attached to the sensor material or platform and to release energy following nanocrystal excitation;

a source of up-converting antibody nanocrystal excitation energy; and a detection device for detecting energy released by the plurality of nanocrystals following excitation.

2. The system of claim 1 further including a rinsate adapted to remove unbound nanocrystals and particles from the microfluidic channel.

3. The system of claim 2 wherein the system further includes an upstream flow path adapted to deliver the rinsate and the plurality of up-converting antibody nanocrystal sensing probes or markers to the microfluidic channel.

4. The system of claim 3 wherein the sensor material or platform comprises a fiber-based material.

5. The system of claim 4 wherein the fiber based material comprises a polymer thread, the polymer thread further being coated with a hydrogel matrix containing the plurality of capture or sensing antibodies adapted to attach to the target bio-organisms.

6. The system of claim 5 further including an aperture disposed intermediate the cross channel and the microfluidic channel.

7. The system of claim 6 including an impact zone wherein air samples containing aerosol particles and bio-organisms of interest impact and adhere to the hydrogel matrix containing the plurality of capture or sensing antibodies.

8. The system of claim 1 wherein the source of up-converting antibody nanocrystal excitation energy comprises laser energy device.

9. The system of claim 1 wherein the source of up-converting antibody nanocrystal excitation energy comprises a broadband light emitting diode (LED).

10. The system of claim 9 wherein each the target bio-organisms include a plurality of epitopes.

11. The system of claim 10 wherein the system is structured and arranged to identify a single bio-organism by identifying multiple epitopes associated therewith.

12. A method for the detection of target bio-organisms in aerosols, the method comprising the steps of:

a. identifying a size range of a target bio-organism particle or particles;

b. removing particles and other materials outside the size range of the target bio-organism, whereby a plurality of test samples are created;

c. concentrating the plurality of test samples into a spatially-confined and controlled particle beam;

d. directing the confined and controlled particle bean into a microfluidic channel formed in a particle trap assembly;

e. impinging the confined and controlled particle beam on a refreshable sensor material or platform: the sensor material including a plurality of capture or sensing antibodies adapted to attach to the target bio-organisms in the particle trap assembly whereby a portion of the target bio-organism particles in the plurality of test samples are immobilized in the refreshable sensor material;

f. introducing a plurality of preselected up-converting antibody nanocrystal sensing probes or markers to the microfluidic channel;

g. binding at least one of the plurality of preselected up-converting antibody nanocrystal sensing probes or markers to a respective one of the portion of the target bio-organism particles in the plurality of test samples are immobilized in the refreshable sensor material;

h exposing the plurality of up-converting antibody nanocrystal (UNC) sensing probes or markers to a source of up-converting antibody nanocrystal excitation energy; and i. detecting energy released by the plurality of nanocrystals following excitation.

13. The method of claim 12 further including the step of rinsing the plurality of test samples immobilized in the refreshable sensor material adapted to remove unbound target bio-organism particles.

14. The method of claim 13 wherein the step of rinsing is repeated to remove unbound nanocrystal sensing probes and target bio-organisms from the microfluidic channel following the step of binding with a rinsate adapted to remove unbound nanocrystal sensing probes and target bio-organisms from the microfluidic channel.

15. The method of claim 12 including the step of refreshing the sensor material or platform, whereby a plurality of unbound capture or sensing antibodies adapted to attach to the target bio-organisms are introduced to a portion of the target bio-organism particles in another of the plurality of test samples.

16. The method of claim 15 wherein the step of refreshing the sensor material or platform is performed on a plurality of microfluidic channels formed in one or more particle trap assemblies aligned in series.

17. The method of claim 15 wherein the step of refreshing the sensor material or platform is performed on a plurality of microfluidic channels formed in one or more particle trap assemblies aligned in parallel.

18. The system of claim 1 wherein the source of up-converting antibody nanocrystal excitation energy comprises laser energy device.

* * * * *